United States Patent
Clement et al.

(10) Patent No.: US 12,163,947 B2
(45) Date of Patent: Dec. 10, 2024

(54) METHOD AND SYSTEM FOR CHARACTERIZING UNDEBARKED WOODEN LOGS AND COMPUTING OPTIMAL DEBARKING PARAMETERS IN REAL TIME

(71) Applicant: BID GROUP TECHNOLOGIES LTD., Prince George (CA)

(72) Inventors: Francis Clement, Blainville (CA); Guy Morissette, Lorraine (CA)

(73) Assignee: BID GROUP TECHNOLOGIES LTD, Prince George (CA)

( * ) Notice: Subject to any disclaimer, the term of this patent is extended or adjusted under 35 U.S.C. 154(b) by 638 days.

(21) Appl. No.: 17/445,974

(22) Filed: Aug. 26, 2021

(65) Prior Publication Data
US 2022/0065841 A1    Mar. 3, 2022

Related U.S. Application Data (60) Provisional application No. 63/070,887, filed on Aug. 27, 2020.

(51) Int. Cl.
*G01N 33/46* (2006.01)
*B27L 1/00* (2006.01)
(Continued)

(52) U.S. Cl.
CPC ............... *G01N 33/46* (2013.01); *B27L 1/00* (2013.01); *G06F 18/214* (2023.01);
(Continued)

(58) Field of Classification Search
CPC .................................. B27L 1/00; G01N 33/46
See application file for complete search history.

(56) References Cited

U.S. PATENT DOCUMENTS

| 6,072,890 A | 6/2000 | Savard et al. |
| 6,137,894 A | 10/2000 | Ahonen et al. |

(Continued)

FOREIGN PATENT DOCUMENTS

| CA | 2780202 A1 | 12/2013 |
| EP | 2282196 A1 | 2/2011 |

(Continued)

OTHER PUBLICATIONS

Spinelli et al., Efficient Debarking to Increase Value Recovery in Small-Scale Forestry Operations, Jan. 27, 2018, Small-scale Forestry, vol. 17, p. 377-392 (Year: 2018).*

(Continued)

*Primary Examiner* — Mi'schita' Henson
(74) *Attorney, Agent, or Firm* — Brouillette Legal Inc.; Philippe Brouillette (57) ABSTRACT

A method for characterizing undebarked wooden logs and computing optimal debarking parameters in real time is provided. The method comprises a scanning device upstream of a debarker for providing data, usually in the form of images, to a deep learning algorithm model. The model may be trained with human assistance or not to detect and identify, with an acceptable amount of certainty, characteristics of undebarked logs. The characteristics are used in an optimization software and classified in an index table. The index table is used to determine optimized parameters for debarking the log.

18 Claims, 4 Drawing Sheets

(51) Int. Cl.
   *G06F 18/21* (2023.01)
   *G06F 18/214* (2023.01)
   *G06F 18/40* (2023.01)
   *G06N 20/00* (2019.01)

(52) U.S. Cl.
   CPC ............ *G06F 18/217* (2023.01); *G06F 18/41* (2023.01); *G06N 20/00* (2019.01)

(56) References Cited

U.S. PATENT DOCUMENTS

| | | |
|---|---|---|
| 6,526,154 B1 | 2/2003 | Taipale et al. |
| 7,819,148 B2 | 10/2010 | Rinfret et al. |
| 8,215,347 B2 | 7/2012 | Brdicko et al. |
| 8,509,491 B2 | 8/2013 | Giuiceandrea |
| 9,063,094 B2 | 6/2015 | Benoit et al. |
| 9,588,098 B2 | 3/2017 | Gagne |
| 10,099,400 B2 | 10/2018 | Gagnon et al. |
| 2005/0072494 A1* | 4/2005 | Price .................. G05B 15/02 700/167 |
| 2013/0333805 A1* | 12/2013 | Gagnon ............. G01N 21/8986 144/357 |
| 2020/0088711 A1* | 3/2020 | More .................. H04N 23/57 |

FOREIGN PATENT DOCUMENTS

| | | | |
|---|---|---|---|
| WO | 199107653 A1 | 5/1991 | |
| WO | WO-2018169712 A1 * | 9/2018 | ............. G01N 33/46 |

OTHER PUBLICATIONS

Helppelmann et al., Development and Validation of a Photo-Based Measurement System to Calculate the Debarking Percentages of Processed Logs, 2019, Remote Sensing, 11(9), 1133, pp. 1-16 (Year: 2019).*

* cited by examiner

METHOD AND SYSTEM FOR CHARACTERIZING UNDEBARKED WOODEN LOGS AND COMPUTING OPTIMAL DEBARKING PARAMETERS IN REAL TIME

CROSS-REFERENCE TO RELATED APPLICATIONS

The present patent application claims the benefits of priority of commonly assigned U.S. Provisional Patent Application No. 63/070,887, entitled "METHOD FOR CHARACTERIZING UNBARKED WOODEN LOGS AND COMPUTING OPTIMAL DEBARKING PARAMETERS IN REAL TIME" and filed at the United States Patent and Trademark Office on Aug. 27, 2020.

FIELD OF THE INVENTION

The present invention generally relates to the field of characterising an undebarked wooden log by deep learning AI models, upstream from a debarking device in order to adjust, in real time, said device and obtain an optimal debarking. Adjusting the debarking device entails finding the optimal inline and rotational speed as well as cutting tools pressure applied on a given log. An optimal debarking process will minimize fiber loss and residual bark on logs.

BACKGROUND OF THE INVENTION

Debarking process is very important in industrial wood transformation. Since bark is not a desired component in wood chips, it is preferably removed at the beginning of any log processing into lumber products. Moreover, the bark contains a lot of silica which deteriorates the saw blades quickly. The debarking process generally comprises removing a thin outer layer on the logs called bark (inner and outer), usually with a debarker, while being careful not to remove the healthy underlying wood fibres. Thus, the debarking efficiency influences the profitability of the mill. Removal of too much wood fibers as well as creation of external damages on logs ends up in lower volume yields and, consequently, financial lost. Furthermore, other industries like pulp and paper industries are using residual wood chips from sawmilling as raw material for their production. Any content in bark among the chips is then considered as a lost as it cannot be used or at least limited to a very small amount into paper pulp (1%-1.5% depending on the season). It is common practice for chip buyers to pay less or even reject material containing more than a certain amount of bark.

Inventions such as those disclosed in U.S. Pat. No. 6,526,154 B1 are useful for determining debarking quality but are useless for adjusting the debarker in real time when the wood species or moisture content of incoming logs varies, for example.

Debarking process optimisation is a very complex task. It requires detailed knowledge of the incoming material and knowledge of the control of the debarking devices in order to decrease fiber loss and remaining bark quantity. Debarking parameters such as rotational speed and tools pressure are related to the intrinsic characteristics of the logs. Yet, there may be important variations in log characteristics depending on some environmental factors such as moisture content, species, temperature, etc. These factors greatly influence the ease of debarking. Such factors contribute to complexify the optimisation of the debarking process. It is well known in the industry that sorting wooden logs upstream of the debarker comprises operational and financial benefits. Manually sorting the logs by species, for example, may be done on the logging site as well as in the mill's lumber yard. However, such processes are demanding, costly and time consuming. These processes are especially pushed to their operational limits when log characterizing and debarking is required to be as fast as possible while simultaneously maintaining an acceptable debarking quality for operational and financial benefits and requirements.

The U.S. Pat. No. 9,588,098 B2 discloses an optical method for subdividing images into a plurality of small squares for which a plurality of texture statistics is calculated. The U.S. Pat. No. 9,588,098 B2 calculates Local Binary Patterns (LBPs) and histogram and performs statistical analysis and classification based on LBPs and histogram. The statistics are transformed into vectors which are then classified by a simple neural network, a support vector machine (SVM), a multivariate linear model, a static gain matrix, etc. The classification processing is carried out for the calculated vectors associated with all image regions, resulting in a set of probable species indications. Such classic texture methods are not as accurate as newer deep learning AI techniques. Larger crops used by AI are more prone to give a better identification with their more global views statistically speaking. Small local texture images of U.S. Pat. No. 9,588,098 B2 may not all contain special characteristics of a species for instance.

Some other techniques for wood species identification are known in the art. Such techniques typically involve chemical reaction on wood such as disclosed in U.S. Pat. No. 6,072,890, microscopic inspections, UV radiation (U.S. Pat. No. 9,063,094 B2) or infra-red radiation (U.S. Pat. No. 5,406,378) to name a few. The latter being not possible due to bark presence on logs.

Another apparatus and method shown in U.S. Pat. No. 8,215,347 B2 comprises a mechanical surface scraper used to determine optimal operating parameters of the debarker. The disclosed apparatus, operating in a harsh environment such as debarker infeed conveyor, is hard to implement, having a reliability and ruggedness issues.

To sum up, the prior art methods are either far from being applicable in real time or too complicated to implement in a real production environment of unbarked wooden logs.

Traditionally, human judgement was the only way to adjust the settings of debarkers. A system such as the one disclosed in the U.S. Pat. No. 10,099,400 B2 titled "Method and System for Detecting the Quality of Debarking at the surface of a Wooden Log" discloses measuring the efficiency of debarking downstream of the debarker. Such systems provide data of the process and use such data to adjust said debarker accordingly either by human intervention or automated process. As such system is located downstream of the debarker, the system presents hints on what should have been performed during the debarking process. In the last years, some feedback systems have been deployed to help the sawmillers in the debarking process. The main drawback of the prior art feedback systems, however, is that they cannot predict sudden unexpected changes in the incoming undebarked logs. The results of such systems are only adequate for steady lines of production having a low variation in log characteristics. Any change in the parameters applied to the debarker as a result of a drop in debarking quality is not guaranteed to be optimal for upcoming logs with significantly different characteristics.

Thus, there is a need for a method for characterized undebarked wooden logs and for computing optimal debarking parameters in real time.

SUMMARY OF THE INVENTION

The shortcomings of the prior art can be mitigated by providing an efficient log characterization method upstream from the debarking system that may allow automatic adjustment of the debarker.

Provided may be the computer-implemented method for characterizing an undebarked log in real time, the method comprising the steps of measuring attributes of the undebarked log; identifying characteristics of the undebarked log based on measured attributes of the undebarked log using a trained deep learning model; computing operating parameters of a debarker based on the identified characteristics; and sending the computed operating parameters to the debarker. The measurement of the attributes of the undebarked log may be using a scanning device. The measurement of the attributes of the undebarked log may be using one or more sensors.

In another aspect of the invention, the identification of the characteristics of the log further may comprise one or a combination of any of the following steps, identifying the species of the log; measuring the moisture level of the log; and calculating an intensity of knot presence on the log. The computation of operating parameters may further comprise retrieving operating parameters associated with the identified characteristics. The operating parameters may be indexed in a table having operating parameters associated with one or more log characteristics. The indexation of the log operating parameters may consider the intensity level of the one or more log characteristics.

In another aspect of the invention, the trained deep learning model may be trained comprising the steps of selecting a representative sample of a plurality of logs having identifiable characteristics; scanning the plurality of logs to obtain scan data of the logs; identifying with a deep learning algorithm software of the deep learning model the identifiable characteristics of the logs based on the scan data; analysing the identified characteristics of the logs to output an identification score; and considering the deep learning model trained if the identification score is different from a predetermined value. The deep learning model may be automatically trained by using the measured attributes of the undebarked log for the analysis of the identified characteristics of the logs to output the identification score. The deep learning model may be manually trained with training data and human validations for the analysis of the identified characteristics of the logs to output an identification score. The measured attributes of the undebarked log may further be comprising external data to the undebarked log.

Another embodiment provided may be a system for characterizing an undebarked log in real time, the system comprising a log measurement device for identifying attributes of the undebarked log; a characterizing unit in communication with the log measurement device, the characterizing unit comprising a deep learning model; and a computerized device configured to identify characteristics of the undebarked log based on measured attributes of the undebarked log using the deep learning model; a debarker optimizer in communication with the characterizing unit, the debarker optimizer being configured to compute operating parameters of a debarker based the characteristics identified by the characterizing unit; and a debarker controller in communication with the debarker optimizer and the debarker, the debarker controller being configured to control the debarker using the computed operating parameters from the debarker optimizer.

In another aspect of the invention, the deep learning model may be trainable. The deep learning model may be automatically trainable with the measured attributes of the undebarked log. The deep learning model may be manually trainable with sample logs having identifiable characteristics and with human intervention. The characteristics identified by the characterizing unit may be indexed in a table comprising operating parameters associated with one or more identifiable log characteristics. The characterizing unit may take into account the intensity levels of the identified log characteristics when indexing the characteristics in the table. The system may further comprise one or more lighting device for illuminating the undebarked log when identified by the log measurement device. The system may further comprise external sensors identifying attributes external to the undebarked log, the attributes external to the undebarked log being used by the debarker optimizer. The log measurement device may be any one or a combination of a line scanner, an area scan camera or an infrared camera.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which.

DETAILED DESCRIPTION OF THE PREFERRED EMBODIMENT

A novel system and method for characterizing undebarked wooden logs and computing optimal debarking parameters in real time will be described hereinafter. Although the invention is described in terms of specific illustrative embodiments, it is to be understood that the embodiments described herein are by way of example only and that the scope of the invention is not intended to be limited thereby. The term undebarked is used to describe a log that comprises bark and that has not been debarked yet. Accordingly, the term unbarked is used to describe a log comprising no bark that has been debarked.

Figure 1:
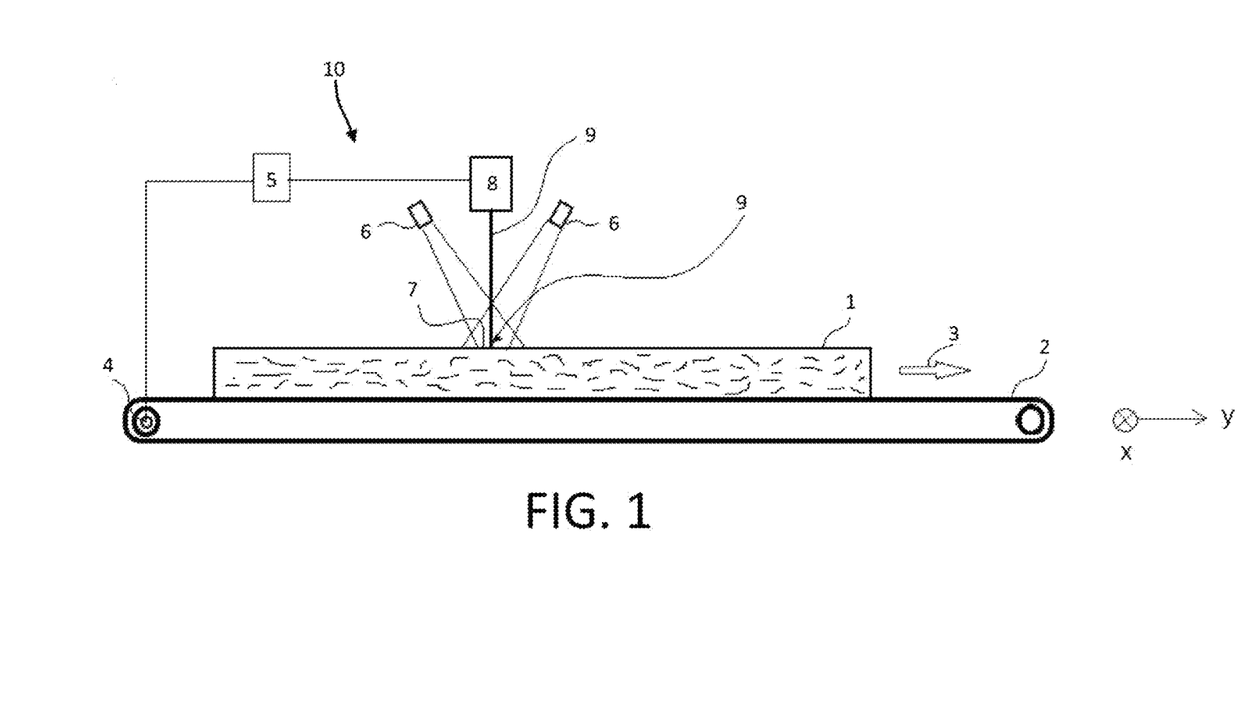
FIG. 1 is an elevation side view of an embodiment of a system for characterizing barked wooden logs and computing optimal debarking parameters in real time in accordance with the principles of the present invention.

Referring to FIG. 1, an exemplary embodiment of a system for characterizing wooden logs having bark 10 is shown. A wooden log having bark 1 is conveyed, typically using a conveyor 2, towards direction 3, generally referred as the Y axis. The system 10 comprises an encoder 4 that determines coordinates and/or position of the conveyor belt 2. The system further comprises a data acquisition unit 5, typically embodied as a computerized device 5. The data acquisition unit 5 may comprise a transient memory unit, a central processing unit (CPU), a storage unit and a network unit. The encoder 4 is in direct communication with the data acquisition unit 5 to communicate the determined coordinates and/or position of the conveyor belt 2.

Figure 2:
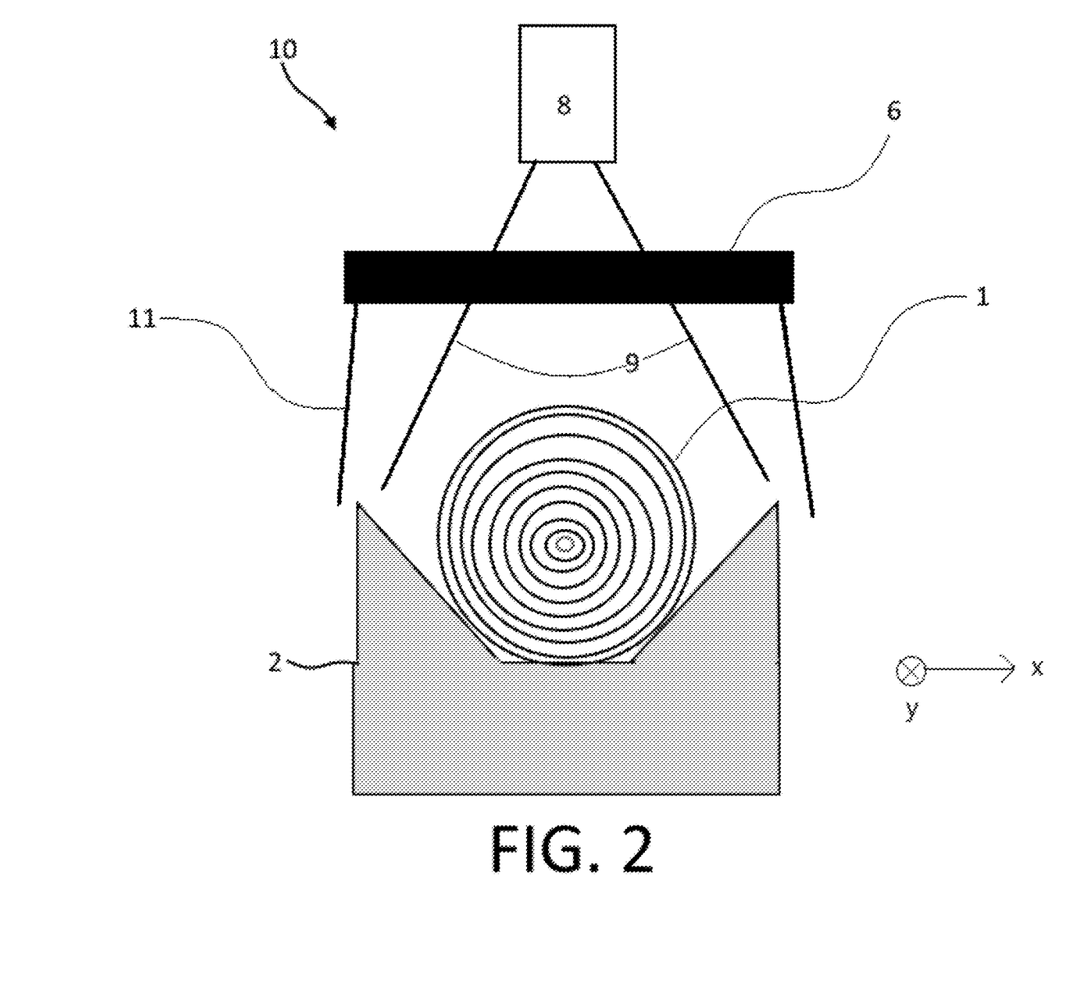
FIG. 2 is an elevation front view of the system of FIG. 1.

The conveyor 2 may be any type of conveyor known in the art. The conveyor 2 may comprise a flat surface, a curved surface as shown at FIG. 2, or a supporting surface made of chains, a rubber surface, etc.

The system 10 may further comprise one or more lighting devices 6. The lighting device may be configured to illuminate a region/area 7 of the surface of the log with bark 1. The system further comprises a scanning device 8. The light from the lighting device is reflected on the outer surface of the log 1 and captured by the scanning device 8. The reflected light may reach the scanning device 8 through a field of view 9 of the scanning device 8. Accordingly, the illuminated region 7 of the log 1 may be scanned by the scanning device 8 and the scanned information is communicated to the data acquisition unit 5. Understandably, any type of scanning device 8 may be used for scanning the undebarked log 1 and may be for example a line scan, an area scan camera or an infrared camera.

The scanned data may be color and/or grayscale images of partial or complete external surface of the undebarked wooden log 1. The scanning device 8 is typically positioned to capture/scan the log 1 while moving towards a debarker or bark removing unit, not shown. The captured images are transmitted to the data acquisition unit 5 through a network or through a wire. The data acquisition unit 5 is programmed to perform a real-time analysis of the received image data. To determine characteristics of the undebarked logs 1, such as species, type, quality, freshness (moisture level), sap level, quantity of knots, and so on, the data acquisition unit 5 may be programmed to execute one or more deep learning models algorithms using the collected data from the scans as input.

The system 10 may further comprise a parameter index or table. Such table generally comprises specific operating parameters of the debarker associated with a range of characteristics of the log. The operating parameters of the debarker may comprise, but are not limited to, conveying speed, rotational speed, level of pressure to be applied by the tools on the outer surface of the undebarked log, tool aperture size, etc. The measured characteristics of the undebarked logs 1 may comprise, but are not limited to, surface temperature of the log 1, species of the wood, humidity level and special features, such as knots, kink or protuberances, presence/absence of moisture or of blue stain, diameter or shape of the log. As will be discussed in more details, the characteristics of the log 1 may be measured or calculated using different means, not shown, such as capturing color images using a sensor or camera or using different sensors measuring the said characteristics of the log 1.

Referring now to FIG. 2, a front view of the system 10 of FIG. 1 is shown. As shown, the round end of the log 1 rests on the conveyor 2. The conveyor 2 is moving the log 1 towards the Y axis 3 (as illustrated in FIG. 1). At least one lighting device 6, embodied as a light diffuser, is positioned above the conveyed log 1. The field of light 11 created by the lighting device 6 is delimited on each side of the conveyed log 1. The scanning device 8 captures one or more images of the conveyed log 1 through the field of view 9 of the said scanning device 8. Understandably, both the lighting device and the scanning device 8 may be positioned over, on the side or under the undebarked log 1, as long as the scanning device 8 has a field of view of the log 1.

In other embodiments, the system 10 may further comprise a plurality of lighting devices 6. In such embodiments, the lighting devices 6 may be positioned or disposed anywhere radially around the undebarked log 1. Each field of light 11 of their respective lighting device 6 are combined to partially or completely illuminate the undebarked log 1, at least to cover the scanned field of view 9.

Figure 3:
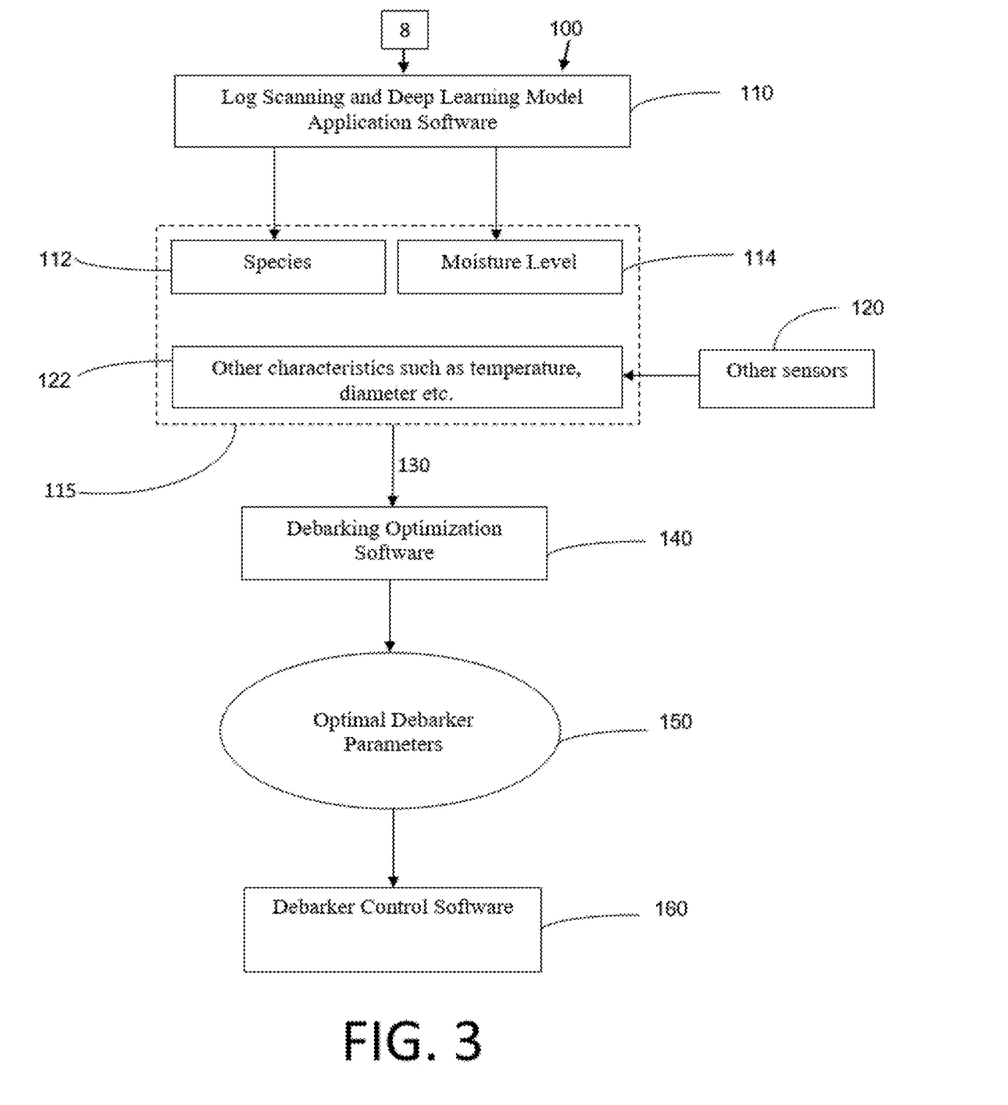
FIG. 3 is a schematic view of an embodiment of a data processing flow for characterizing barked wooden logs and computing optimal debarking parameters in real time in accordance with the principles of the present invention.

Referring now to FIG. 3, an embodiment of a system to control operations of a debarker 100 is illustrated. The system 100 is configured to receive data from the one or more scanning devices 8 or sensors, not shown, such as images of the surface of the undebarked logs 1. The system 100 generally comprises a deep learning model application software 110, also referred to as deep learning, artificial intelligence or AI model, a debarking optimization software 140, log characterizing module 115 and a debarking control software 160.

The log scanning and deep learning model application software 110 is programmed to identify the characteristics of the conveyed log 1. The log scanning and deep learning model application software 110 is in data communication with the scanning device and sensors, such as camera, humidity sensors, infra-red sensors, etc. The sensing devices 8 and 120 may feed data to the log scanning application software 110 which determines the characteristics of the log 1. The log scanning and deep learning model application software 110 may be manually trained with training data and human interactions validating the assumptions of the software 110. In other embodiments, the deep learning model application software 110 may be configured to automatically train with real-time data using additional sensors validating the assumptions of the software 110. The deep learning model application software 110 uses the trained deep learning model to identify, characteristics of the log, such as be not limited to species 112 and moisture level 114. In some embodiments, the system 110 further comprises other external sensors 120 adapted to measures or identify other characteristics 122 such as log temperature, diameter, etc. The external sensors 120 may measure characteristics which are external to the log, such as weather, humidity level, temperature or characteristics which are particular to the log 1, such as moisture level of the log 1. For example, the external sensors 120 may be weather sensors providing data about atmospheric conditions. In some embodiments, the system 10 may be connected with third party systems through a network, such as the Internet. In such embodiments, external data such a historical temperature or weather data associated with the logs or the environment where the log 1 growth may be used to identify characteristics of the log 1.

The outputted or identified characteristics 130 of the log 1 are inputted in the optimization software 140. The optimization software 140 is programmed to compute optimal debarking parameters 150 based on the characteristics of the log 1 identified by the log scanning software 110. The optimal debarking parameters 150 are inputted in the debarker control software 160. The debarker control software 160 is connected or in communication with the debarker (not shown) and controls the operations of a debarker.

In some embodiments, the optimization software 140 has access or comprises a table of debarking parameters, not shown, associated with characteristics of the log or with ranges of values of the characteristics of the log. As discussed above, the control parameters may comprise debarker rotation speed, conveying speed, tools pressure, tool aperture size, etc. The optimization software 140 may be configured to fetch the operating parameter of the debarker associated with one or more values of the characteristics of the logs. In some embodiments, combination of intensity levels of identified characteristics may require different optimized debarking parameters 150. As an example, a log having a high moisture level and a high number of knots by square inch may be associated with a reduced speed of rotation of the tools compared to a log having a low moisture level and a low number of knots by square inch which may require an increased speed or rotation of the tools. The optimization software 140 may thus, in real time, adjust the debarking parameters 150 in view of the received characteristics 130 of the log to be debarked. The optimal debarking parameters 150 may be any parameter of a debarking apparatus known in the art, such as pressure of the tools, rotational speed, said rotational speed possibly varying lengthwise of the log, advancing speed of the log, pressure on the rollers, etc.

Figure 4:
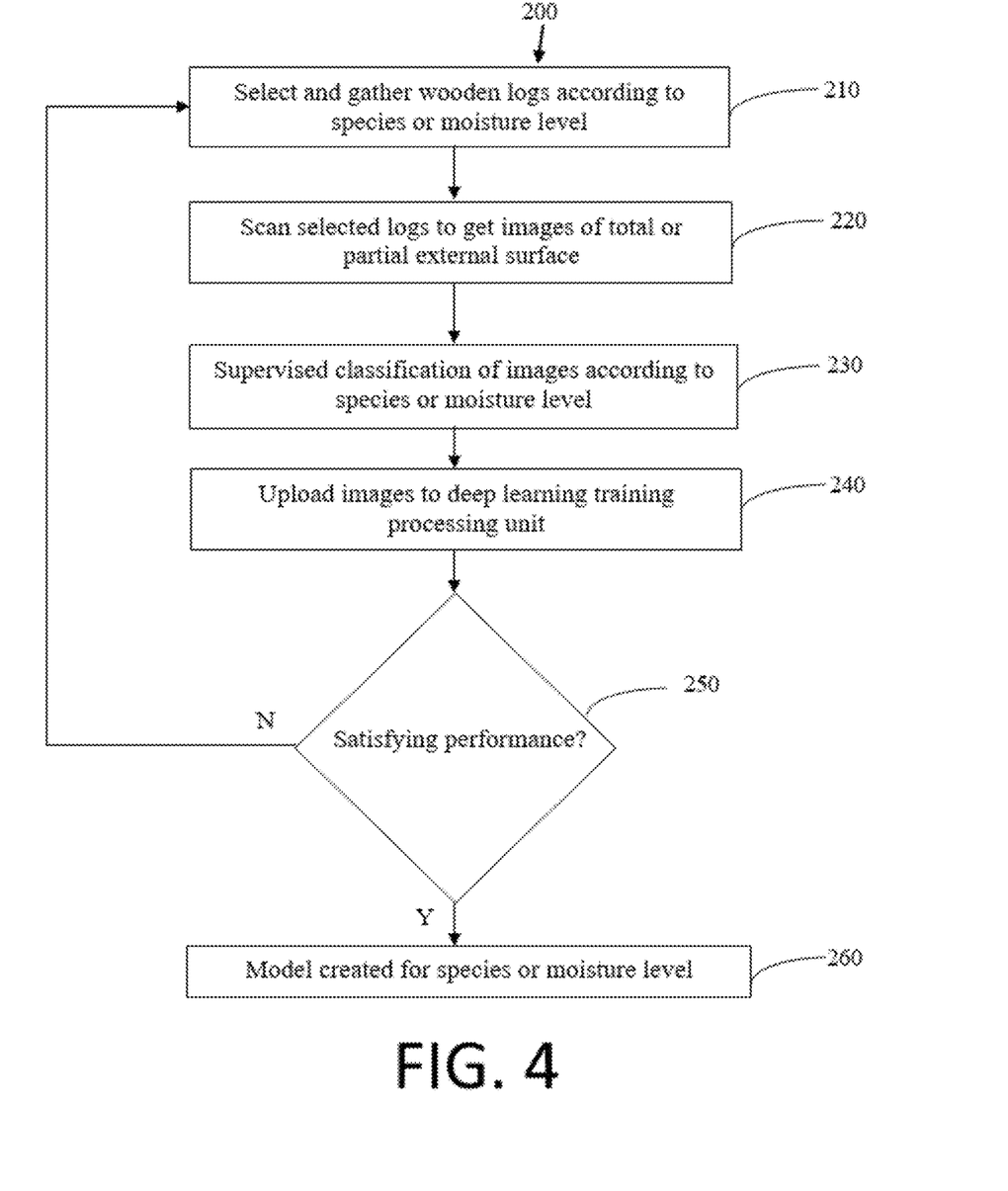
FIG. 4 is a schematic representation of an embodiment of a learning process for a given model for characterizing wooden logs having bark and computing optimal debarking parameters in real time in accordance with the principles of the present invention.

Now referring to FIG. 4, an embodiment of a method 200 for building a deep learning model for a given characteristic is shown. The method generally comprises selecting and gathering wooden logs according to characteristics of the log, such as but not limited to identified species and moisture level 210, scanning selected logs to capture images of the outer surface of the log, either partially or completely 220, classifying the captured images according to characteristics of the log, such as species or moisture levels 230 and communicating the captured images to the deep learning training unit 240. The method 200 further comprise testing the performance of the trained model 250. If the performances are equal or above a predetermined level, the model is created for the tested characteristics 260. If the performances are under the predetermined level, the method 200 is executed another time with different parameters, at least until the predetermined levels are achieved.

The selection of wooden logs 210 generally comprise picking a representative sample of a plurality of logs of having similar and/or different characteristics to be identified. As an example, and as shown in FIG. 4, logs may be selected according to the species and moisture levels of logs. Thus, logs of the sample may be grouped into categories regarding the parameters of debarking based on the species or moisture levels of the selected logs. For example, a first group of logs may comprise fir logs and a second group having pine and spruce logs. When an appreciable or representative number of logs has been gathered, the logs may be scanned by a scanning system 220.

The deep learning algorithm may be configured to learn with or without human assistance 230. In embodiments without human intervention, the deep learning algorithm may learn by itself with repetition and may detect characteristics or combination of characteristics that could possibly be unnoticed by human operators. This embodiment may both provide unexpectedly good or bad results and mostly depends on the quality of the model used.

In embodiments using human intervention, intervention by at least an operator may be used to classify and tag the data, usually in the form of images, of the scanned logs from the sample according to the chosen characteristic. The deep learning algorithm may therefore comprise a frame of reference to selected desired characteristics. For example, an operator may apply paint on certain logs having certain characteristics and may verify if the identified logs are correctly characterised by the algorithm. The amount of human intervention may vary based on the quality and/or capacity of the model and may be reduced over time. It may further be possible to set up the intervention of a human only when outlying or abnormal data is received.

The classified and scanned images are sent to a deep learning processing software unit 240 proceeding with the learning and which may thus output an identification score on the characteristics of the sample data 250. If the score is satisfying, the model may be considered ready and used for determined log characteristics in production 260. Otherwise, if the score is not satisfying, the operator may provide or reassess already established learning parameters of the deep learning processing software and/or gather more samples and start the process.

Various algorithms may be used to determine if a score is satisfying or not. For example, the score may be required to be above a certain level to be satisfying. It may be noted that any type of deep learning algorithm may be used with the method of the present invention and is not limited to one type only. In an embodiment of the invention, more than one model of deep learning algorithms may be used. The model to be used may be determined based on the received data from the scanning device. For example, a model may be preferable for certain log characteristics wherein it may not be preferable for other log characteristics wherein another model may be preferable.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A computer-implemented method for characterizing an undebarked log in real time, the method comprising:
    performing a contactless characterization of the undebarked log;
    identifying characteristics of the undebarked log based on the characterization of the undebarked log using a trained deep learning model;
    computing operating parameters of a debarker based on the identified characteristics; and
    sending the computed operating parameters to the debarker,
    wherein the computation of operating parameters further comprises retrieving operating parameters associated with the identified characteristics.

2. The method of claim 1, the characterization of the undebarked log using a scanning device.

3. The method of claim 1, the characterization of the undebarked log using one or more sensors.

4. The method of claim 1, the identification of the characteristics of the log further comprising one or a combination of any of the followings:
    identifying the species of the log;
    measuring the moisture level of the log; and
    calculating an intensity of knot presence on the log.

5. The method of claim 1, the operating parameters being indexed in a table having operating parameters associated with one or more log characteristics.

6. The method of claim 5, the indexation of the log operating parameters taking into account the intensity level of the one or more log characteristics.

7. The method of claim 1, the trained deep learning model being trained comprising the steps of:

selecting a representative sample of a plurality of logs having identifiable characteristics;

scanning the plurality of logs to obtain scan data of the logs;

identifying with a deep learning algorithm software of the deep learning model the identifiable characteristics of the logs based on the scan data;

analysing the identified characteristics of the logs to output an identification score; and considering the deep learning model trained if the identification score is different from a predetermined value.

8. The method of claim 7, the deep learning model being automatically trained by using the characterization of the undebarked log for the analysis of the identified characteristics of the logs to output the identification score.

9. The method of claim 1, the deep learning model being manually trained with training data and human validations for the analysis of the identified characteristics of the logs to output an identification score.

10. The method of claim 1, the characterization of the undebarked log further comprising external data to the undebarked log.

11. A system for characterizing an undebarked log in real time, the system comprising:

a contactless log characterization sensor for identifying attributes of the undebarked log;

a characterizing unit in communication with the contactless log characterization sensor, the characterizing unit comprising:

a deep learning model; and a computerized device configured to identify characteristics of the undebarked log based on measured attributes of the undebarked log using the deep learning model;

a debarker optimizer in communication with the characterizing unit, the debarker optimizer being configured to compute operating parameters of a debarker based the characteristics identified by the characterizing unit; and a debarker controller in communication with the debarker optimizer and the debarker, the debarker controller being configured to control the debarker using the computed operating parameters from the debarker optimizer, wherein the characteristics identified by the characterizing unit are indexed in a table comprising operating parameters associated with one or more identifiable log characteristics.

12. The system of claim 11, the deep learning model being trainable.

13. The system of claim 12, the deep learning model being automatically trainable with the measured attributes of the undebarked log.

14. The system of claim 12, the deep learning model being manually trainable with sample logs having identifiable characteristics and with human intervention.

15. The method of claim 11, the characterizing unit taking into account the intensity levels of the identified log characteristics when indexing the characteristics in the table.

16. The system of claim 11, the system further comprising one or more light sources for illuminating the undebarked log when identified by the log measurement device.

17. The system of claim 11, the system further comprising external sensors identifying attributes external to the undebarked log, the attributes external to the undebarked log being used by the debarker optimizer.

18. The system of claim 11, the log measurement device being any one or a combination of a line scanner, an area scan camera or an infrared camera.

* * * * *